US006239244B1

(12) United States Patent
Stepp et al.

(10) Patent No.: US 6,239,244 B1
(45) Date of Patent: May 29, 2001

(54) POLYSILOXANE COMPOUND WHICH IS STABLE DURING STORAGE AND PRODUCES VULCANISATES WHICH CAN BE PERMANENTLY WETTED WITH WATER

(75) Inventors: Michael Stepp; Johann Bindl; Gerhard Kreis, all of Burghausen; Arnold Garhammer, Simbach, all of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/380,942

(22) PCT Filed: Mar. 12, 1998

(86) PCT No.: PCT/EP98/01412

§ 371 Date: Sep. 13, 1999

§ 102(e) Date: Sep. 13, 1999

(87) PCT Pub. No.: WO98/41579

PCT Pub. Date: Sep. 24, 1998

(30) Foreign Application Priority Data

Mar. 18, 1997 (DE) .............................................. 197 11 314

(51) Int. Cl.$^7$ .................................................... C08G 77/08
(52) U.S. Cl. ................................ 528/15; 528/26; 528/25; 528/29; 523/109; 524/862
(58) Field of Search ................................ 528/15, 26, 25, 528/29; 524/862; 523/109

(56) References Cited

U.S. PATENT DOCUMENTS

| 5,367,001 | * | 11/1994 | Itoh et al. ............................. 523/109 |
| 5,580,924 | | 12/1996 | Stepp et al. . | |
| 5,849,812 | * | 12/1998 | Zech et al. ........................... 523/107 |

FOREIGN PATENT DOCUMENTS

| 0 398 745 | 11/1990 | (EP) . |
| 0 480 238 A1 | 4/1992 | (EP) . |

OTHER PUBLICATIONS

Derwent Abstract corresponding to EP 480238 AN 92–124540.

* cited by examiner

*Primary Examiner*—Margaret G. Moore
(74) *Attorney, Agent, or Firm*—Brooks & Kushman P.C.

(57) ABSTRACT

The invention concerns polysiloxane compounds which contain the following components: 1. organopolysiloxane with at least two aliphatic double bonds in the molecule; 2 organopolysiloxane with at least two Si—H groups in the molecule; 3. noble metal catalyst; and 4. hydrophilic modifier of general formula (I) $[H_2C=CH-A^1-(A^2)_m-X]_nB$ (I), in which $A^1$, $A^2$, X, B, m and n have the meanings given in claim 1. The polysiloxane compounds are stable during storage and are used as dental casting compounds.

11 Claims, No Drawings

POLYSILOXANE COMPOUND WHICH IS STABLE DURING STORAGE AND PRODUCES VULCANISATES WHICH CAN BE PERMANENTLY WETTED WITH WATER

The present invention relates to polysiloxane materials which have a long shelf life and, after vulcanization, give permanently water-wettable elastomers and the use of said materials as dental impression compounds.

Polysiloxane materials which vulcanize to give elastomers are widely used as impression compounds. The addition-crosslinking systems have proven particularly useful since they set more rapidly and, in contrast to the condensation-crosslinking systems, do not require large amounts of problematic catalyst.

A major disadvantage of silicone impression preparations based on hydrophobic polysiloxanes is due to the fact that it is scarcely possible to take an accurate impression of moist surfaces, such as tissue surfaces, tooth surfaces or surfaces of dentures, in the oral cavity since the moisture contents accumulate in the form of drops between the surface of which an impression is to be taken and the impression compound.

A surface-active impression compound causes the moisture on the surfaces of which an impression is to be taken to spread to give a thin moisture film. As a result, cavities in the impression are avoided and a precise reproduction of the surface structure is achieved.

For example, EP-A-480 238 discloses addition-crosslinking water-wettable silicone impression compounds which contain special alkoxylated fatty alcohol or a methylated or acylated alkoxylated fatty alcohol. However, owing to the poor binding in the impression compounds, the surface-active agents are extracted in contact with aqueous media. Thus, the water wettability is lost through, for example, rinsing with water, disinfection, sterilization, preparation of duplicates with the aid of water-containing impression preparations, such as plaster, before the desired aims of the application, such as reproducible wetting properties of the silicone impression after removal from the moist surface, are achieved.

EP-A-398 745 describes polysiloxane materials which give permanently water-wettable vulcanized products and contain hydrophilic modifiers incorporatable by crosslinking. The hydrophilic modifiers are polysiloxanes which contain hydrophilic alkylene ether groups and either aliphatic double bonds or Si—H groups. The hydrophilic modifiers described in EP-A-398 745 contain a noble metal catalyst as a result of their preparation. In addition, the hydrophilic modifiers preparable to date and containing double bonds have small amounts of Si—H groups and the hydrophilic modifiers preparable to date and containing Si—H groups have small amounts of double bonds.

When used as hydrophilic modifiers, the known copolymers, owing to the deficiencies described above, do not give mixtures having a long shelf life, either with the two-component rubber component (A), which comprises a polysiloxane material having aliphatic double bonds and a noble metal catalyst, or with the component (B) which comprises polysiloxane material having Si—H groups. In all cases, proportions of vulcanized product form during storage.

The separate storage of the hydrophilic modifier is not a satisfactory remedy since a three-component polysiloxane material is too difficult to handle when used in practice.

US-A-5,580,921 likewise describes polysiloxane materials which give permanently water-wettable vulcanized products and have, as hydrophilic modifiers, polysiloxanes incorporatable by crosslinking. The modifier is obtained free of platinum by a very complicated preparation process, in which high-boiling intermediates of the modifier are distilled. The shelf life is improved as a result.

It is the object of the present invention to provide polysiloxane materials which give permanently water-wettable elastomeric vulcanized products and whose components have a particularly long shelf life.

The invention relates to polysiloxane materials having a long shelf life, giving permanently water-wettable elastomeric vulcanized products and containing the constituents
1. organopolysiloxane having at least two aliphatic double bonds in the molecule,
2. organopolysiloxane having at least two Si—H groups in the molecule,
3. noble metal catalyst and
4. hydrophilic modifier of the general formula I $$[H_2C=CH-A^1-(A^2)_m-X]_nB \qquad (I),$$

in which
$A^1$ denotes a divalent $C_2$–$C_{10}$-hydrocarbon radical which may be substituted by halogen atoms,
$A^2$ denotes a divalent $C_1$–$C_{24}$-hydrocarbon radical which may be interrupted by non-neighboring oxygen atoms or nitrogen atoms or the groups of the formulae —NR—, —CO— or —CO—NR$^1$— and may additionally be substituted by halogen atoms, with the proviso that at least 5 carbon atoms are present per oxygen or nitrogen atom,
x denotes a divalent group —O—, —CO— or —COO—,
B denotes polar radicals which have carbon atoms and at least 2 non-neighboring oxygen atoms, the oxygen atoms being present as ether oxygen or in hydroxyl groups, $C_1$–$C_4$-acyl groups or $C_1$–$C_3$-trialkylsilyl groups, with the proviso that not more than 3 carbon atoms are present per oxygen atom,
m denotes the values 0 or 1,
n denotes integral values from 1 to 50,
R and $R^1$ each denote a monovalent $C_1$–$C_{10}$-hydrocarbon radical which may be substituted by halogen atoms.

The polysiloxane material having a long shelf life is very readily water-wettable both before and after vulcanization. The wettability of the vulcanized products remains good even after relatively long contact with aqueous systems, for example after sterilization.

By mixing the constituents 1 to 4, preferably 2 components are prepared, namely the component A which contains the catalyst constituent 3 and all constituents except for constituent 2 and component B which contains all constituents except for constituent 3.

Preferably, all components contain hydrophilic modifiers. In this embodiment, the total amount of hydrophilic modifier in the polysiloxane material having a long shelf life can be considerably increased and hence the hydrophilic properties considerably enhanced without separation occurring. A further advantage of this embodiment is that the hydrophilic modifier may be present in both components homogeneously and in the same concentration. With the use of modern application forms, such as double-chamber cartridges with mounted static mixer, this is very important owing to the very short mixing times.

The divalent $C_2$–$C_{10}$-hydrocarbon radical $A^1$ has a hydrophobic character. It may be saturated, aliphatically unsaturated, aromatic, linear or branched. Preferably, $A^1$ has 3 to 8 carbon atoms.

The divalent $C_1$–$C_{24}$-hydrocarbon radical $A^2$ has a hydrophobic character. It may be saturated, aliphatically unsaturated, aromatic, linear or branched. The oxygen atoms or nitrogen atoms or groups of the formulae —NR—, —CO— or —CO—$NR^1$— may be part of a linear chain or of heterocycles. Preferably, $A^2$ has 5 to 18 carbon atoms.

—O— and —COO— are preferred as divalent group X, in particular —COO—.

Preferably, B has at least 2, in particular at least 3, oxygen atoms. Preferably, B has not more than 50, in particular not more than 20, oxygen atoms.

The polar radical B is preferably composed of polyethylene glycol units [—$CH_2$—$CH_2$—O—] with preferably 1–20 alkylene units, in particular with 3–10 alkylene oxide units, or a polyol having 3 to 10 carbon atoms, such as glycerol and sorbitol, or a sugar radical, such as glucose and sucrose. B may contain both free OH groups and acylated, silylated or alkylated OH groups.

The acylated OH groups are preferably acylated with formic or acetic acid. The trialkylsilyl groups are preferably trimethylsilyl groups. The alkylated OH groups are preferably ethoxy or in particular methoxy groups.

n indicates the number of unsaturated units [$H_2C$=CH—$A^1$—$(A^2)_m$—X] forming a molecular bond with B. n preferably has integral values from 1 to 10.

R and $R_1$ are preferably alkyl radicals having from 1 to 6 carbon atoms, in particular the methyl, ethyl, n-propyl and isopropyl radicals.

Preferred halogen atoms as substituents of $A^1$, $A^2$, R and $R^1$ are fluorine, chlorine and bromine atoms.

Examples of hydrophilic modifiers are:

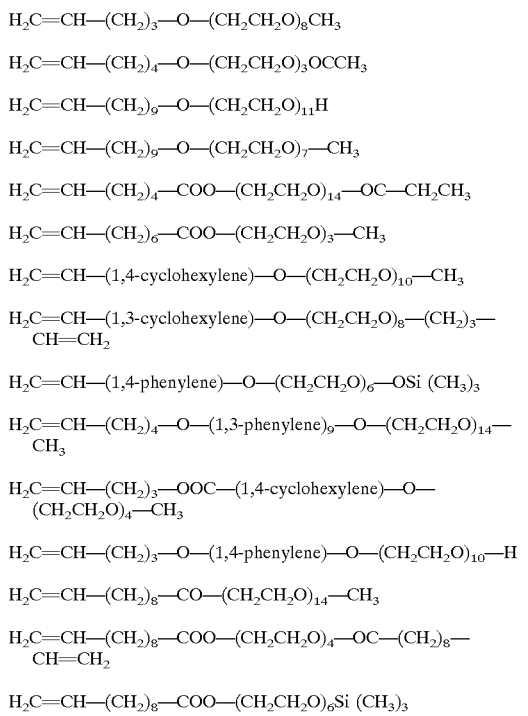

Sorbitan mono-10-undecanoate
Sorbitan mono-10-undecanoate, peracetylated
Sorbitan bis-10-undecanoate
Pentaerythrityl mono-10-undecanoate
Pentaerythrityl bis-10-undecanoate, trimethylsilylated
and mixtures thereof.

Particularly preferred hydrophilic modifiers are the 10-undecanoic acid esters, in which [$H_2C$=CH—$A^1$—$(A^2)_m$—X] in the general formula I is $H_2C$=CH—$(CH_2)_8$—COO. These have antibacterial activity. This effect is particularly advantageous during use in the dental sector because the not inconsiderable risk of infection by the hardened molding can be reduced thereby.

The hydrophilic modifiers are in some cases commercially available and are prepared by generally customary methods of organic synthetic chemistry.

The polysiloxane materials preferably contain at least 0.1% by weight, in particular at least 0.5% by weight, and preferably not more than 5.0% by weight, in particular not more than 10.0% by weight, of hydrophilic modifier.

Constituent 1, namely organopolysiloxane having at least two aliphatic double bonds in the molecule, is preferably an organopolysiloxane which has SiC-bonded $C_1$–$C_6$-alkyl radicals, in particular methyl radicals, and/or phenol radicals, and at least two $C_1$–$C_6$-alkenyl radicals per molecule, which contain the aliphatic double bonds. Preferred alkenyl radicals are vinyl radicals and allyl radicals. Preferably, a molecule contains not more than 10 alkenyl radicals. The organopolysiloxanes 1 are preferably linear.

The viscosity of the organopolysiloxanes 1 depends on the desired viscosity of the formulated pastes or mechanical profile of the moldings preparable therewith and is preferably 300 to 200,000 mPa.s at 20° C.

Constituent 2, namely organopolysiloxane, having at least two Si—H groups in the molecule, preferably comprises organpolysiloxanes which, in addition to Si—H groups, have SiC-bonded $C_1$–$C_6$-alkyl radicals, in particular methyl radicals and/or phenyl radicals. The organpolysiloxanes 2 are preferably linear. Preferably, a molecule contains not more than 10, in particular not more than 5, Si—H groups.

The viscosity of the organopolysiloxanes 2 is preferably 20 to 50,000 mpa.s, in particular 100 to 5000 mpa.s, at 20° C.

The polysiloxane materials may crosslink if at least one of the constituents 1, 2 or 4 has at least 3 crosslinkable groups, namely Si—H groups or aliphatic double bonds.

Constituent 3, namely noble metal catalyst, preferably consists of platinum metals and/or compounds thereof, in particular platinum and/or compounds thereof. It is possible here to use all catalysts which have also been used to date for the addition reaction of Si—H groups with aliphatically unsaturated compounds. Examples of such catalysts are metallic and finely divided platinum, which may be present on supports, such as silica, alumina or active carbon, compounds or complexes of platinum, such as platinum halides, e.g. $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6 \cdot 6H_2O$ and cyclohexanone, platinum-siloxane complexes, such as platinum-vinylsiloxane complexes, in particular platinum-divinyltetramethyldisiloxane complexes with or without a content of detectable inorganically bonded halogen, bis(gamma-picoline)platinum dichloride, trimethylenedipyridineplatinum(II) dichloride, dicyclopentadienylplatinum dichloride, dimethylsulfoxyldiethyleneplatinum(II) dichloride and reaction products of platinum tetrachloride with olefin and primary amine or secondary amine or primary and secondary amine, such as the reaction product of platinum tetrachloride, dissolved in 1-octene, with sec-butylamine, or ammonium-platinum complexes. Platinum complexes which are prepared from $H_2PtCl_6$ are particularly preferred.

Noble metal catalyst 3 is preferably used in amounts of 0.5 to 500 ppm by weight (parts by weight per million parts by weight), in particular 2 to 400 ppm by weight, calculated in each case as elemental platinum and based on the total weight of the organopolysiloxanes present in the constituents 1 and 2.

Most of the abovementioned platinum catalysts are so active that an inhibitor which, after mixing of the components, prevents premature crosslinking to give the elastomer is preferably added as constituent 5 to the polysiloxane materials. Examples of inhibitors 5 are acetylenically unsaturated alcohols, such as 3-methyl-1-butyn-3-ol, 1-ethynylcyclohexan-1-ol, 3,5-dimethyl-1-hexyn-3-ol and 3-methyl-1-pentyn-3-ol, and vinylsiloxane-based inhibitors, such as 1,1,3,3-tetramethyl-1,3-divinylsiloxane and poly-, oligo- and disiloxanes containing vinyl groups.

The polysiloxane materials preferably contain at least 0.01% by weight, in particular at least 0.1% by weight, and preferably not more than 3.0% by weight, in particular not more than 0.5% by weight, of inhibitor 5.

The polysiloxane materials may contain, as constituent 6, organopolysiloxanes which have neither Si—H groups nor aliphatic double bonds. Organopolysiloxanes which are liquid at 20° C. are preferred, in particular polydimethylsiloxanes terminated with a trimethylsilyl group and having a preferred viscosity of 50 to 100,000 mPa.s at 20° C.

The polysiloxane material may contain, as constituent 7, fillers, such as nonreinforcing fillers, i.e. fillers having a BET surface area of up to 50 $m^2/g$, such as quartz, cristobalite, diatomaceous earth, calcium silicate, zirconium silicate, montmorillonites, such as bentonites, zeolites, including the molecular sieves, such as sodium aluminum silicate, metal oxide powders, such as aluminas or zinc oxides or mixtures thereof, barium sulfate, calcium carbonate, gypsum, glass powder and plastic powder; reinforcing fillers, i.e. fillers having a BET surface area of more than 50 $m^2/g$, such as pyrogenically prepared silica, precipitated silica and mixed silicon-aluminum oxides having a large BET surface area. Said fillers may have been rendered hydrophobic, for example by treatment with organosilanes or organosiloxanes, or by etherification of hydroxyl groups to alkoxy groups. It is possible to use one type of filler or a mixture of at least two fillers. The content of constituent 7 in the polysiloxane materials is preferably 10 to 80% by weight.

The polysiloxane materials may contain colorants as constituent 8. Colorants 8 are used, for example, for distinguishing between different components and for monitoring the mixing. Examples of colorants 8 are inorganic and organic colored pigments, such as titanium dioxide or aluminum spinels, such as cobalt aluminum spinel. The preferred content of constituent 8 in the polysiloxane materials is not more than 10% by weight.

The polysiloxane materials may contain, as constituent 9, additives for specific purposes. Suitable additives are fungicides, bactericides, algicides, microbicides, odor substances, flavors, corrosion inhibitors and, although not preferred, organic solvents. The polysiloxane materials contain additives in each case preferably in amounts of 0.001 to 1% by weight, in particular of 0.01 to 0.1% by weight.

In the mixed pasty or flowable state, the polysiloxane materials have a good affinity for moist surfaces, such as the moist dentine and enamel and the moist gums, and are therefore particularly suitable as impression compounds in dental medicine. Moreover, the aqueous plaster slurry can be poured into the crosslinked impressions in the usual time of 30 minutes after removal of the impression from the patient's mouth without the plaster cast being falsified by the evolution of hydrogen. They can also be used for taking impressions of other body parts, such as the auditory canal, and for all purposes for which silicone elastomers having hydrophilic properties are advantageous, for example contact lenses, prostheses or implants, and nonmedical purposes.

Unless stated otherwise in each case, in the following examples
a) all stated amounts are based on weight;
b) all pressures are 0.10 mPa (abs.);
c) all temperatures are 20° C.;
d) vinyl polymer 1 denotes polydimethylsiloxane having $\alpha$, $\omega$-vinyl groups, having a viscosity of about 7000 $mm^2/s$ according to Brookfield at 25° C.;
e) crosslinking agent means anhydrous diorganopolysilxane having dimethylhydrogensiloxane units as terminal units and comprising dimethylsiloxane units and methylhydrogensiloxane units, wherein 10 dimethylsiloxane units are present per methylhydrogensiloxane unit, having a viscosity of 150 mpa.s at 25° C.;
f) catalyst denotes a Pt-1,3-divinyl-1,1,3,3-tetramethylsiloxanyl complex,
g) inhibitor denotes dimethylsiloxane having an average 5 to 10 dimethylsiloxane units and $\alpha$, $\omega$-vinyl groups;
h) HT denotes hardening time;
i) RH denotes relative humidity.

EXAMPLES

Example 1

Preparation of a hydrophilic modifier of the general formula I 50 g of 10-undecenoyl chloride and 25 g of polyethylene glycol 200 (Hoechst AG, Gendorf) were stirred at 80° C. until the end of the gas evolution. After the addition of 1 g of hexamethyldisilazane for reducing the residual acid and OH content, a vacuum was applied and heating was carried out at 80° C./4 hPa. The residue was filtered over 1 g of Seitz Super® filter aid. 55.7 g of a clear, yellowish liquid were isolated, which, according to $^1$H-NMR spectrum, was the bis-10-undecanoic acid ester of polyethylene glycol 200 (molar undecenoic acid radical : ethylene glycol ratio= 2:4.3).

Comparative Example 1

Preparation of a hydrophilic modifier not incorporatable by crosslinking, analogously to Example 1

44.5 g of dodecenoyl chloride and 22.2 g of polyethylene glycol 200 (Hoechst AG, Gendorf) were stirred at 80° C. until the end of the gas evolution. After the addition of 1 g of hexamethyldisilazane for reducing the residual acid and OH content, a vacuum was applied and heating was carried out at 80° C./4 hPa. The residue was filtered over 1 g of Seitz Super® filter aid. 47.9 g of a clear, yellowish liquid were isolated, which, according to $^1$H-NMR spectrum, was the bisdodecanoic acid ester of polyethylene glycol 200 (molar dodecenoic acid radical : ethylene glycol ratio=2:4.6).

Example 2

Extraction experiments on mixtures with the modifier from Example 1, with the non crosslinkable modifier from Comparative Example 1 and with a starting mixture Three mixtures were prepared:
1. Dental silicone impression compound, components A+B, analogous to U.S. Pat. No. 5,580,921, Example 4, but without hydrophilic modifier 2. Dental silicone impression compound of above mixture 1 with additionally 3% by weight of hydrophilic modifier according to the invention, from Example 1
3. Dental silicone impression compound of mixture 1 with additionally 3% by weight of hydrophilic modifier not according to the invention, from Comparative Example 1.

Each of these mixtures was hardened by mixing the components A and B at room temperature. After storage for 4 days at room temperature, the vulcanized products were extracted in a Soxhlet apparatus with a mixture of 75% by weight of toluene and 25% by weight of 1,2-dimethoxyethane (monoglyme) for 7 hours under reflux conditions and, after complete removal of the solvent residues, were reweighed in vacuo.

The following fractions were extracted:

Mixture 1: 2.7% by weight
Mixture 2: 4.4% by weight
Mixture 3: 5.5% by weight

From this it is possible to calculate that, in contrast to the dodecanoic acid derivative of Comparative Example 1, which is extractable to an extent of 93%, the 10-undecenoic acid derivative according to the invention, from Example 1, is incorporated by crosslinking during hardening to an extent of 44%.

For the comparative testing of the effect and the long-term stability of dental compounds with different hydrophilic modifiers, the "hydrophobic" base dental compound with A and B components was prepared (="blank value").

In comparison with the measured blank value of the hydrophobic material, the hardening times of the corresponding hydrophilic dental compounds at 37° C. were also determined. Hydrophilic modifier of Example 1 and hydrophilic modifier analogous to U.S. Pat. No. 5,580,921, Example 1, based on organosiloxane, were each tested in the A component. The use of the hydrophilic modifier in the A component is of great interest owing to the higher long-term stability of the stored modifier-free B component which is then to be expected.

Example 3 a) Preparation of a Dental Compound "Lightbody" (A component)

| | |
|---|---|
| Vinyl polymer | 56% |
| Quartz powder having a particle size of 1–30 μm (Quarzwerke Frechen) | 38% |
| HDK ® H15 (from Wacker-Chemie GmbH) | 4% |
| Chrome oxide green pigment | 0.3% |
| $TiO_2$ pigment | 0.2% |
| Catalyst | 1.4% |
| Inhibitor | 0.1% |
| | 100.0% | b) Preparation of a Dental Compound "Lightbody" (B Component)

| | |
|---|---|
| Vinyl polymer | 41% |
| Quartz powder having a particle size of 1–30 μm (Quarzwerke Frechen) | 39% |
| HDK ® H15 (from Wacker-Chemie GmbH) | 4% |
| Chrome oxide green pigment | 1% |
| Crosslinking agent | 15% |
| | 100% | c) Mixing of 4% of Hydrophilic Modifier of Example 1 into the A Component According to Example 3a)

d) Mixing of 4% of Hydrophilic Modifier Analogous to U.S. Pat. No. 5,580,921, Example 1, into the A Component According to Example 3a)

The A components according to Examples 3c) and 3d) were stored at 23° C. as well as subjected to accelerated thermal aging at 70° C. (21 and 42 days, respectively). The hydrophobic base component A according to Example 3a, likewise "aged" according to the scheme, served as the blank value.

For the determination of the respective hardening times at 37° C., all A components were tested with a B component stored only at room temperature, in the A:B ratio=1:1, using a Cyclovisco Brabender apparatus at 37° C.

Hardening times at 37° C. of hydrophilic dental compound A+B (A:B =1:1) compared with "blank value" (=hydrophobic material) in seconds:

| Storage conditions 23° C./50% RH | 4% of modifier from Example 1 HT 37° C. | 4% of modifier analogous to US-5,580,921 HT 37° C. | Blank value HT 37° C. |
|---|---|---|---|
| 1 day 23° C. | 235 | 135 | 130 |
| 21 days 23° C. | 220 | 135 | 130 |
| 42 days 23° C. | 215 | 140 | 125 |
| 21 days 70° C. | 200 | 270 | 110 |
| 42 days 70° C. | 215 | 410 | 90 |

Result:
1. The modifier of Example 1 resulted only in a slight decrease in the HT 37° C. in the A component on thermal aging for 3 weeks (=21 days) and 6 weeks (=42 days). After 42 days at 70° C., the measured value of 215 sec is still lower than in the first test after 1 day at 23° C.
2. The material with modifier analogous to U.S. Pat. No. 5,580,921in the A component is initially stable at 23° C. (HT 370C =135 sec), but the values after storage at 70° C. then indicate a doubling of the HT 37° C. to 270 and 410 sec, respectively.

Example 4

Determination of the Degree of Incorporation by Crosslinking of Various Hydrophilic Modifiers into Dental Compounds Modifier extraction for determining the degree of incorporation by crosslinking of the novel hydrophilic modifier of Example 1. For this purpose, samples of vulcanized product were subjected to a Soxhlet extraction analogously to Example 2. 525 ml of toluene and 175 ml of ethynylglycol dimethyl ether were used as the solvent mixture. Extraction was carried out for 5 hours.

Samples

1. Blank value: Dental compound "Lightbody A component" from Example 4a, but with 0.5% catalyst. Dental compound "Lightbody B component" from Example 3b, but with 4% of crosslinking agent with 0.14% by weight of H.
2. Dental compound "Lightbody B component" from Example 3a, but with 0.5% of catalyst and 4% of hydrophilic modifier of Example 1. Dental compound "Lightbody B component" from Example 3b, but with 4.0% of crosslinking agent with 0.14% by weight of H and 4% of hydrophilic modifier of Example 1.
3. Dental compound "Lightbody A component", 0.5% of catalyst, +4% of hydrophilic modifier analogous to U.S. Pat. No. 5,580,921 Dental compound "Lightbody B component", 4% of crosslinking agent with 0.14% by weight of H and 4% of hydrophilic modifier analogous to U.S. Pat. No. 5,580,921.

Result:

|  | Sample 1 | Sample 2 | Sample 3 |
|---|---|---|---|
| Loss of mass | 1.7% | 3.1% | 3.9% |
| Difference from blank value: | — | 1.4% | 2.2% |
| Degree of incorporation of hydrophilic modifier by crosslinking | — | 65% | 45% |

Example 5

Determination of the Hydrophilicity Before and After Storage of the Samples of Example 4 in Water The samples were stored in water for 7 days and then dried for 3 days at 23° C.

Contact angle Sample 1 Sample 2 Sample 3 (after storage in water) 87° 60° 65°

Result: The hydrophilicity is still good in the case of sample 2 after storage in water and confirms the high degree of incorporation by crosslinking (=permanent hydrophilicity).

What is claimed is:

1. An addition-crosslinkable polysiloxane material having a long shelf life, which cures to form permanently water-wettable elastomeric vulcanized products, comprising:

a) one or more organopolysiloxanes having at least two aliphatic double bonds in the molecule, b) one or more organopolysiloxanes having at least two Si—H groups in the molecule, c) at least one noble metal catalyst, and d) one or more hydrophilic modifier(s) of the general formula I

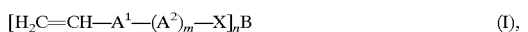   (I), in which $A^1$ denotes a divalent $C_2$–$C_{10}$-hydrocarbon radical which may be substituted by halogen atoms, $A^2$ denotes a divalent $C_1$–$C_{24}$-hydrocarbon radical which may be interrupted by non-neighboring oxygen atoms, nitrogen atoms, or groups of the formulae —NR—, —CO— or —CO—NR$^1$, and may additionally be substituted by halogen atoms, with the proviso that at least 5 carbon atoms are present per oxygen or nitrogen atom, X denotes a divalent group —O—, —CO— or —COO—, B denotes a polar radical comprising carbon atoms and at least 2 non-neighboring oxygen atoms, the oxygen atoms being present as ether oxygen, or in hydroxyl groups, $C_1$–$C_4$-acyl groups, or $C_1$–$C_3$-trialkylsilyl groups, with the proviso that not more than 3 carbon atoms are present per oxygen atom, m denotes the values 0 or 1, n denotes integral values from 1 to 50, and R and $R^1$ each denote a monovalent $C_1$–$C_{10}$-hydrocarbon radical which may be substituted by halogen atoms.

2. The polysiloxane material as claimed in claim 1, in the form of 2 components, a first component (1) containing catalyst constitutent c) and other constituents except for constituent b), and a second component (2) which contains all constituents except for catalyst constituent c).

3. The polysiloxane material as claimed in claim 1, in which the polar radical B of constituent d) comprises polyethylene glycol units [—CH$_2$CH$_2$—O—], comprises a polyol having 3 to 10 carbon atoms, or comprises a sugar radical.

4. The polysiloxane material as claimed in claim 2, in which the polar radical B of constituent d) comprises polyethylene glycol units [—CH$_2$CH$_2$—O—], comprises a polyol having 3 to 10 carbon atoms, or comprises a sugar radical.

5. The polysiloxane material as claimed in claim 1, in which, in constituent d), the expression

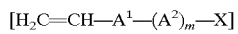

in the general formula (I) is

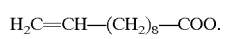

6. The polysiloxane material as claimed in claim 2, in which, in constituent d), the expression

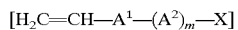

in the general formula (I) is

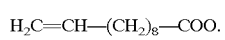

7. The polysiloxane material as claimed in claims 3, in which, in constituent d), the expression

in the general formula (I) i

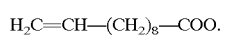

8. The polysiloxane material as claimed in claim 1, which further comprises a hydrosilylation inhibitor as a constituent e).

9. The polysiloxane material as claimed in claim 1, further comprising as a constituent (f), at least one organopolysiloxane which contains neither Si—H groups nor aliphatic double bonds.

10. The polysiloxane material as claimed in claim 1, further comprising at least one filler as a constituent (g).

11. A dental impression material comprising the polysiloxane material of claim 1.

* * * * *